(12) United States Patent
Robles (10) Patent No.: US 12,115,018 B2
(45) Date of Patent: Oct. 15, 2024

(54) STERILE PROBE COVER

(71) Applicant: The United States Government as Represented by the Department of Veterans Affairs, Washington, DC (US)

(72) Inventor: Gerardo Robles, Los Angeles, CA (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 294 days.

(21) Appl. No.: 17/609,044

(22) PCT Filed: May 8, 2020

(86) PCT No.: PCT/US2020/032032
§ 371 (c)(1),
(2) Date: Nov. 5, 2021

(87) PCT Pub. No.: WO2020/227606
PCT Pub. Date: Nov. 12, 2020

(65) Prior Publication Data
US 2022/0192635 A1  Jun. 23, 2022

Related U.S. Application Data

(60) Provisional application No. 62/845,653, filed on May 9, 2019.

(51) Int. Cl.
*A61B 8/00* (2006.01)
*A61B 8/08* (2006.01)
*A61B 8/12* (2006.01)

(52) U.S. Cl.
CPC ............ *A61B 8/445* (2013.01); *A61B 8/0883* (2013.01); *A61B 8/12* (2013.01); *A61B 8/4281* (2013.01)

(58) Field of Classification Search
CPC ......... A61B 8/12; A61B 8/4281; A61B 8/445; A61B 8/4422; A61B 8/0883; A61B 46/10;
(Continued)

(56) References Cited

U.S. PATENT DOCUMENTS 5,299,578 A * 4/1994 Rotteveel ............. G10K 11/355
600/463
5,997,481 A * 12/1999 Adams ................. A61B 8/4281
600/459

(Continued)

*Primary Examiner* — Carolyn A Pehlke
(74) *Attorney, Agent, or Firm* — Ballard Spahr LLP (57) ABSTRACT

An assembly for receiving a transesophageal echocardiogram (TEE) probe comprising a probe shaft having a length can comprise a cover defining an opening at a proximal end and a receiving space in communication with the opening, the receiving space having a length in a longitudinal dimension that is sufficient to receive the length of the probe shaft. A gel capsule can be positioned within the receiving space of the cover. The gel capsule can define a proximal opening and an interior in communication with the proximal opening. The interior of the gel capsule can contain a quantity of gel. Within a plane that is perpendicular to the longitudinal dimension, the interior can have a cross sectional area that is sufficient to receive a distal end of the probe shaft with a clearance to permit contact between the gel within the capsule and an exterior surface of the probe shaft.

18 Claims, 9 Drawing Sheets

(58) Field of Classification Search
CPC ..... A61B 46/13; A61B 46/20; A61B 1/00142; A61B 1/00144
See application file for complete search history.

(56) References Cited

U.S. PATENT DOCUMENTS

| | | | |
|---|---|---|---|
| 2016/0045099 A1* | 2/2016 | Farhadi | A61B 1/00137 600/116 |
| 2016/0113660 A1* | 4/2016 | O'Neil | A61B 17/1322 606/203 |
| 2018/0153387 A1* | 6/2018 | Abitbol | A61B 1/00071 |

* cited by examiner

STERILE PROBE COVER

CROSS-REFERENCE TO RELATED APPLICATION

This application is a U.S. National Phase Application of International Application PCT/US2020/032032, filed May 8, 2020, which claims priority to and the benefit of U.S. Provisional Patent Application No. 62/845,653, filed on May 9, 2019. Each of the entirety of which is above-identified applications is hereby incorporated by reference herein in its entirety.

FIELD

The application relates to sterile probe assemblies and sterile probe covers, and methods of using such sterile probe assemblies and sterile probe covers.

BACKGROUND

A transesophageal echocardiogram (TEE) is a diagnostic procedure that uses a TEE probe to collect sonographic images of a patient's heart. The distal tip of the probe includes an ultrasound transducer that produces and detects ultrasonic waves. The detected waves can be translated into two-dimensional and three-dimensional images that can be displayed on a screen. The TEE probe is typically coated with a lubricant gel and then introduced into the patient's esophagus via the mouth.

SUMMARY

Described herein, in various aspects, is an assembly for receiving a transesophageal echocardiogram probe comprising a probe shaft having a length. The assembly can comprise a cover defining an opening at a proximal end and a receiving space in communication with the opening, the receiving space having a length in a longitudinal dimension that is sufficient to receive the length of the probe shaft. A gel capsule can be positioned within the receiving space of the cover. The gel capsule can define a proximal opening and an interior in communication with the proximal opening. The interior of the gel capsule can contain a quantity of gel. Within a plane that is perpendicular to the longitudinal dimension, the interior can have a cross sectional area that is sufficient to receive a distal end of the probe shaft with a clearance to permit contact between the gel within the capsule and an exterior surface of the probe shaft.

The cover can be configured for selective elongation and retraction in the longitudinal dimension about and between a collapsed configuration and an expanded configuration.

The cover can comprise an accordion fold structure.

The cover can comprise at least one gasket that engages an exterior surface of the gel capsule and is configured to hold the gel capsule in place in the longitudinal dimension with respect to the cover as the probe shaft is removed from the gel capsule.

The gel capsule can further comprise a removable lid.

The assembly can further comprise a locking mechanism configured to secure the assembly to the TEE probe.

The locking mechanism can comprise a band having a pawl at a first end of the band and a plurality of notches spaced along the length of the band, wherein the pawl is configured to engage the notches.

The locking mechanism can comprise a release lever that is configured to disengage the pawl from the notches.

The assembly can further comprise a housing that is coupled to the cover at the proximal end of the cover, wherein the housing defines an interior volume that receives the cover in the collapsed configuration and the gel capsule within the cover.

The assembly can further comprise a guide element that is coupled to the cover at a distal end of the cover. One of the housing and the guide element can comprise a detent, and the other of the housing and the guide element can comprise a catch into which the detent is received so that the housing and guide element are configured to couple to one another via the detent.

The housing can define a cylindrical interior volume that has a length that is approximately the length of the cover in the collapsed configuration.

The assembly can further comprise a locking mechanism, wherein the housing is configured to be coupled to the TEE probe via the locking mechanism.

The locking mechanism can comprise a band having a pawl at a first end of the band and a plurality of notches spaced along the length of the band. The locking mechanism can engage the housing. The housing can be flexible so that the housing can be configured to compress as the band is ratcheted down against the housing and engage the probe.

The housing and the cover can collectively comprise a single monolithic component.

When the cover is in the collapsed configuration, the cover can define an interior volume that is approximately equal to the exterior volume of the gel capsule.

The cover can comprise an outer plastic layer and an inner sterile paper layer.

A probe system can comprise a TEE probe and an assembly as disclosed herein.

A kit can comprise: a plurality of covers, each cover defining an opening at a proximal end and a receiving space in communication with the opening, the receiving space having a length in a longitudinal dimension that is sufficient to receive a length of a shaft of a TEE probe; and a plurality of gel capsules, each gel capsule configured to be positioned within the receiving space of a respective cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the shaft of the TEE probe with a clearance to permit contact between the gel within the capsule and an exterior surface of the shaft of the TEE probe.

The kit can further comprise a TEE probe.

A probe cover for receiving a transesophageal echocardiogram (TEE) probe that comprises a probe shaft having a length can comprise a collapsible structure configured to be expandable from a collapsed configuration to an expanded configuration. The collapsible structure can define an opening at a proximal end and a receiving space in communication with the opening. When the collapsible structure is in the expanded configuration, the receiving space can have a length in a longitudinal dimension that is sufficient to receive the length of the probe shaft. The collapsible structure, when in the expanded configuration, can be configured to receive a gel capsule.

The probe cover can further comprise an elastic member configured to engage the gel capsule to retain the gel capsule within the collapsible structure.

The probe system can be used according to a method comprising: inserting the gel capsule within the receiving space of the cover; inserting at least a distal portion of a shaft of the TEE probe into the interior of the gel capsule; expanding the cover to cover at least a length of the distal portion of the shaft of the TEE probe; retracting the cover to expose the gel capsule and the distal portion of the TEE probe; and moving the gel capsule to expose the distal portion of the TEE probe, wherein the distal portion of the TEE probe is coated with gel from within the interior of the gel capsule.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a detent" can refer to one or more of such detents, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "approximately" one particular value, and/or to "approximately" another particular value. When such a range is expressed, another aspect includes from the one particular value and/or to the other particular value. Similarly, when values are expressed as approximations, by use of the antecedent "approximately," it will be understood that the particular value forms another aspect. It will be further understood that the endpoints of each of the ranges are significant both in relation to the other endpoint, and independently of the other endpoint. Optionally, in some aspects, when values are approximated by use of the antecedent "approximately," it is contemplated that values within up to 15%, up to 10%, up to 5%, or up to 1% (above or below) of the particularly stated value can be included within the scope of those aspects.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Disclosed herein, in various aspects and with reference to FIGS. 1-15, is a sterile probe cover assembly 100. In use, and as further disclosed herein, it is contemplated that the probe cover assembly 100 can eliminate the need for injecting gel or adjusting and securing a bag in the manner required by conventional methods. It is further contemplated that the disclosed sterile probe cover assembly can provide more efficient application of gel to the probe while also ensuring that sterility is maintained. Still further, it is contemplated that the disclosed sterile probe cover assembly can minimize contamination of TEE probes for the safety of patients while also preventing exposure of the patient's bodily fluids (e.g., blood, saliva, and mucus) to medical personnel. The sterile probe cover assembly 100 can further protect the TEE probe's delicate hardware from physical damage. Moreover, the disclosed sterile probe cover assembly 100 can reduce the time required to prepare for a TEE procedure over conventional methods, which can be particularly desirable in emergency situations. Further, the disclosed sterile probe cover assembly 100 and, in particular, the pre-filled gel cartridge 120 as disclosed herein, can provide for more uniform coverage (with gel) than conventional systems, thereby rendering better quality imaging than conventional systems.

Figure 1:
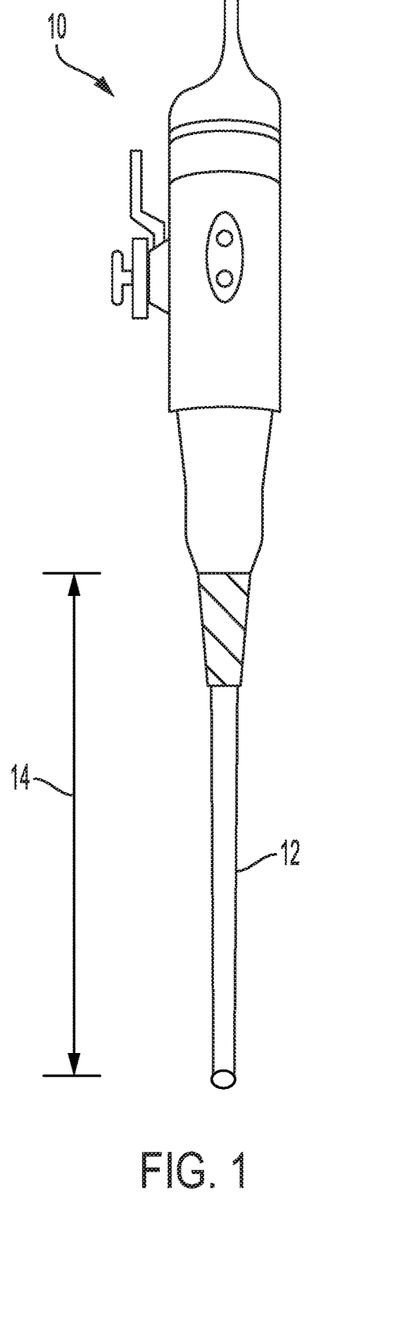
FIG. 1 is a side view of a TEE probe, in accordance with embodiments disclosed herein.
Figure 2:
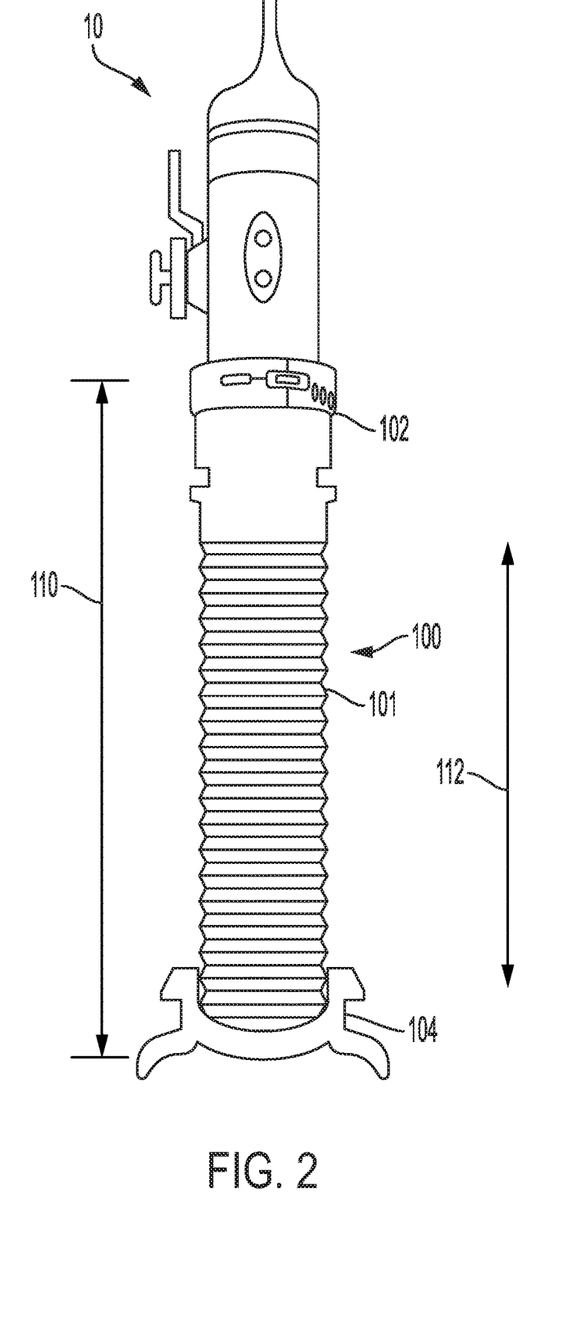
FIG. 2 is a side view of the TEE probe of FIG. 1 partially disposed within an assembly in accordance with embodiments disclosed herein.
Figure 3:
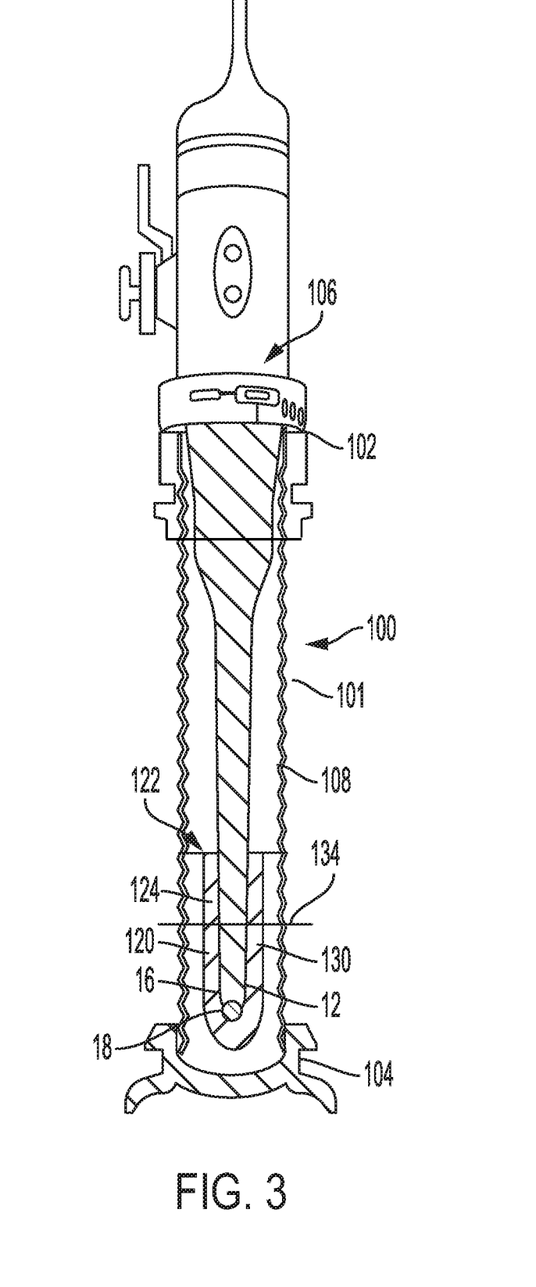
FIG. 3 is the TEE probe and assembly of FIG. 2 with the assembly shown as a partial sectional view.
Figure 4:
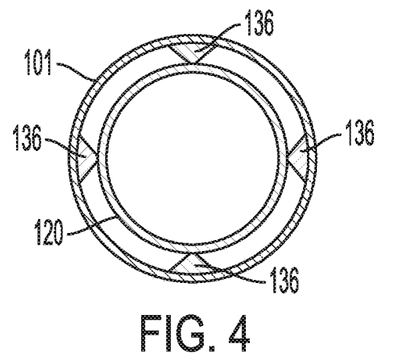
FIG. 4 is a top cross sectional view of the assembly of FIG. 2 including a cover and a gel capsule.
Figure 5:
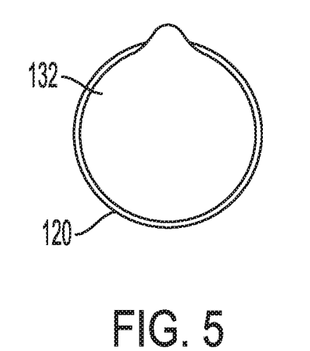
FIG. 5 is a top view of the gel capsule of FIG. 4.
Figure 6:
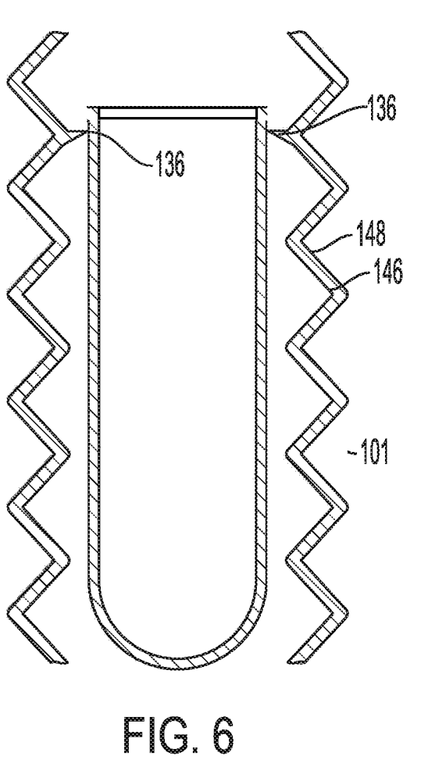
FIG. 6 is a side cross sectional view of the cover and gel capsule as in FIG. 4.
Figure 7:
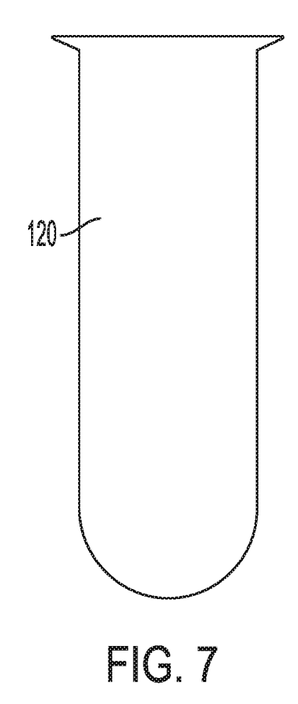
FIG. 7 is a side view of the gel capsule of FIG. 4.
Figure 16:
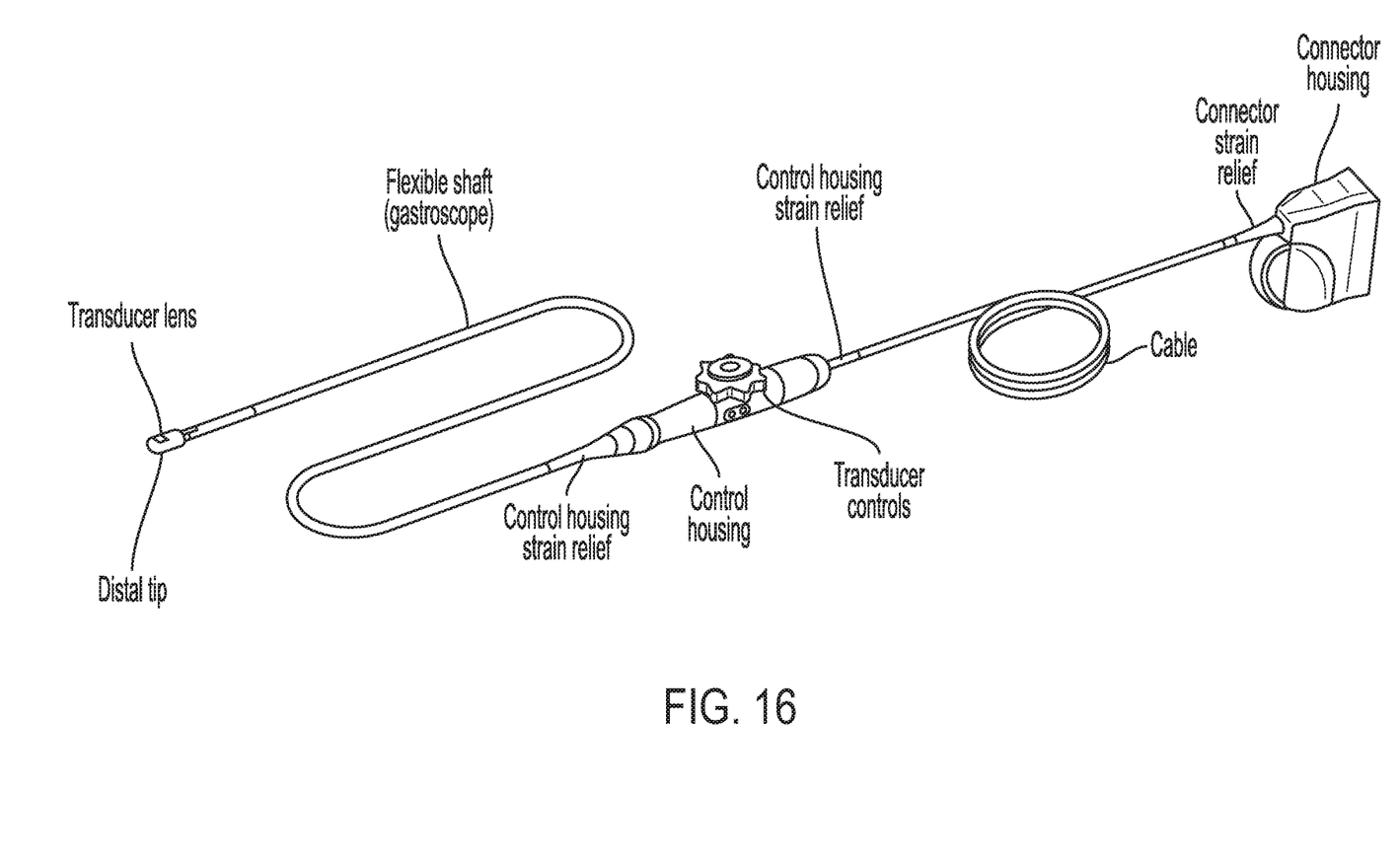
FIG. 16 is a perspective view of a TEE probe in accordance with embodiments disclosed herein.

Referring to FIGS. 1-3, the sterile probe cover assembly 100 can be configured to receive a sterile probe 10 comprising a probe shaft 12, the probe shaft 12 having a length 14. Optionally, the sterile probe 10 can be a TEE probe as is known in the art. An exemplary TEE probe is depicted in FIG. 16. The sterile probe cover assembly 100 can comprise a cover 101 having a proximal end 102 and a distal end 104 that are spaced in a longitudinal dimension 112. The cover 101 can define an opening 106 at the proximal end 102 and a receiving space 108 in communication with the opening 106. The receiving space 108 can have a length 110 in the longitudinal dimension 112 that is sufficient to receive the length 14 of the probe shaft 12.

Referring also to FIGS. 3-7, a gel capsule 120 can be positioned within the receiving space 108 of the cover 101. One or more gaskets 136 can extend radially inward from the cover's inner surface to engage (e.g., bias against) the gel capsule's outer surface in order to hold the gel capsule 120 in place (e.g., via frictional engagement), particularly in the longitudinal dimension with respect to the cover 101 as the probe 10 is removed from the gel capsule. According to some aspects, the gasket 136 can comprise a flexible material that can compress or deflect to receive the outer surface of the gel capsule 120. Optionally, the gasket 136 can comprise a base that attaches to the cover 101 and a tapered distal end (spaced radially inwardly from the base) that engages the gel capsule 120. The gel capsule 120 can define a proximal opening 122 and an interior 124 in communication with the proximal opening 122. The interior 124 of the gel capsule 120 can contain a quantity of gel 130. The gel 130 can be a sterile, water-based lube, such as, for example, SURGILUBE gel. The gel capsule 120 can have a removable lid 132 that can remain on the gel capsule 120 to contain the gel 130 until the sterile probe cover assembly 100 is ready for use. The gel capsule 130 can optionally comprise hard rubber or polymer.

In a plane 134 that is perpendicular to the longitudinal dimension 112, the interior 124 of the gel capsule 120 can have a cross sectional area that is sufficient to receive a distal end of the probe shaft with a clearance to permit contact between the gel within the capsule and an exterior surface 16 of the probe shaft 12. Accordingly, at least a portion of the sterile probe 10 can be inserted into the sterile probe cover 101 and into the gel capsule 124. The clearance can allow a thin gel film or layer to remain on the probe around its entire circumference once the probe is removed. For example, the clearance between the probe shaft 12 and the interior 124 of the gel capsule 120 can be at least one millimeter, two millimeters, or more. According to some embodiments, when the probe shaft 12 is inserted into the gel capsule 120, the gel film can extend up the probe shaft 12 from the distal end by at least four inches, at least five inches, or at least six inches. For example, insertion of the probe shaft into the gel capsule to the distal end of the gel capsule can cause the gel to displace upwardly toward the opening 122 of the gel capsule 120 to a length of at least four, five, or six inches from the distal end of the gel capsule. The gel can act as a medium between the sterile probe 10 and the patient's tissue, thereby promoting optimal image quality.

Referring to FIGS. 2, 6, 10, and 11, the cover 101 can be configured for selective elongation in the longitudinal dimension from a collapsed configuration 140 to an expanded configuration 142. According to at least one aspect, the cover 101 can comprise an expandable structure 144. For example the expandable structure 144 can comprise an accordion fold structure. That is, the cover 101 can comprise a flexible portion that comprises alternating folds so that the cover 101 can be expanded to receive the length 14 of the probe shaft 12. In some embodiments, the entire cover 101 can comprise the expandable structure 144. Optionally, the expandable structure can comprise a sterile cardboard or sterile paper interior layer 146 and a durable outer layer 148, which, in some embodiments, can be plastic. The layer interior layer 146 and outer layer 148 can be bonded or otherwise secured together as is known in the art. The sterile paper interior layer 146 can maintain the sterility of the probe shaft 12, while the durable outer layer 148 can prevent fluid leakage once the probe is extracted from the patient's mouth.

Figure 11:
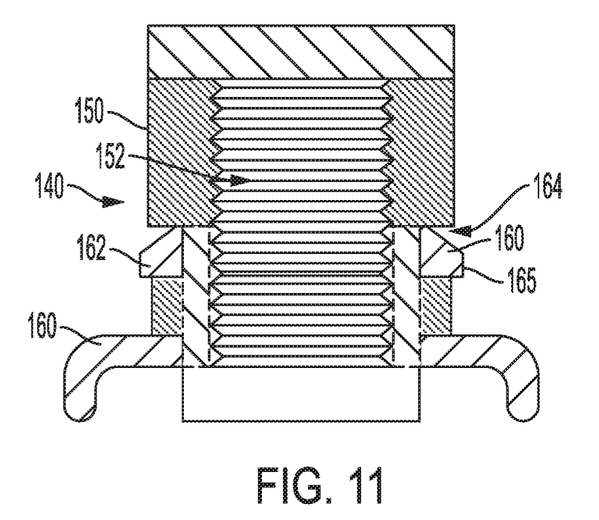
FIG. 11 is a side view of the assembly of FIG. 2 in a collapsed configuration.
Figure 12:
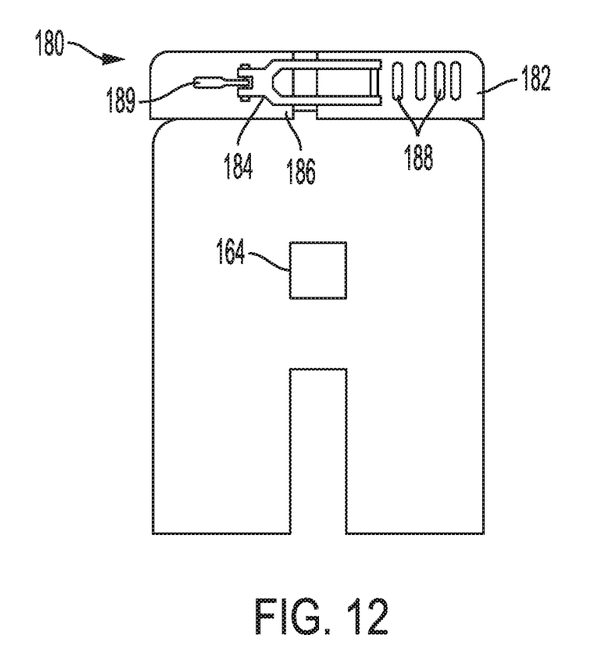
FIG. 12 is a side view of a housing of the assembly of FIG. 2.

Referring to FIG. 11, the sterile probe cover assembly 100 can comprise a housing 150, which can, in some embodiments, comprise hard plastic. The housing 150 can couple to a proximal end of the cover 101. The housing 150 can define an interior volume 152 that can receive the cover 101 in its collapsed configuration. That is, the interior volume 152 of the housing 150 can have a diameter sufficient to receive the maximum outer diameter of the expandable structure 144 as well as the length of the expandable structure 144 when in its collapsed configuration 140. Accordingly, in some embodiments, the interior volume 152 of the housing 150 can receive the cover 101 in the collapsed configuration. Optionally, the cover can receive the gel capsule 120 entirely within the receiving space when in the collapsed configuration 140. Accordingly, the housing's interior volume 152 can optionally be sufficient to receive the gel capsule 120.

Figure 13:
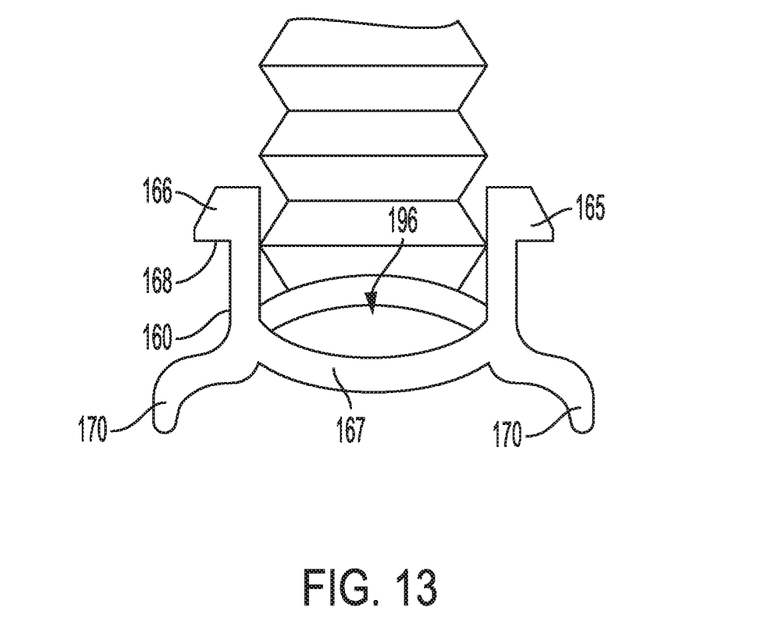
FIG. 13 is a perspective side view of a guide element of the assembly of FIG. 2.

Referring also to FIG. 13, the sterile probe cover assembly 100 can further comprise a guide element 160 that attaches to the distal end 104 of the cover 101. The guide element 160 can act as a grip for a medical professional to pull on and expand the cover 101 from its collapsed configuration 140 to its expanded configuration 142. The guide element 160 can comprise at least one detent that is configured to engage a catch 164 on the housing. As shown, in one exemplary configuration, the at least one detent of the guide element 160 comprises a pair of opposing latches 162 that are configured to engage a pair of complementary catches 164 in the housing 150. Each catch 164 can be a radially extending notch or through hole that is sized to receive at least a portion of a hooked end 165 of the latch 162. The guide element 160 can comprise a flexible material so that the opposing latches 162 can be configured deflect to engage and disengage from respective catches 164. The latches 162 can have a tapered distal end 166 that facilitates coupling to the housing 150. A surface 168 that is perpendicular to the longitudinal dimension 112 can engage a parallel surface of the catch 164 so that a medical professional has to deflect the latches in order to disengage the latches from their respective catches. That is, mere longitudinal force between the housing 150 and the guide element 160 may not decouple the pair.

The latches 162 can extend from a base portion 167 of the guide element 160, and the base portion 167 can attach to cover 101. The latches 162 can have respective lever arms 170 that extend from the base portion 167 in an opposite direction of the hooked end 165 of the respective latch. A medical professional can grip the respective lever arms 170 to deflect the latches 162 from their respective catches 164. In a first embodiment shown in FIGS. 10-11, a medical professional can force the lever arms away from each other (i.e., spread them) to deflect the hooked ends 165 of the respective latches toward each other, thereby disengaging the latches 162 from their respective catches 164. In an alternative embodiment, shown in FIG. 15, a housing 150' can have a pair of opposing latches 162' that are configured in a reverse direction from the embodiment of FIGS. 10-11 so that they deflect outwardly to disengage from catches 164' of the housing 150'. Accordingly, a medical professional can squeeze lever arms 170' together with a thumb and forefinger to release the guide element 160' from the housing 150'. According to various other aspects, the detent can comprise various other attachment devices including a ball detent, clip, other latch style, snap, thread, or any other mechanism for affixing the guide element 160 to the housing 150. Similarly, the catch can comprise any complementary component that engages the detent for releasably affixing the guide element 160 to the housing 150. According to further aspects, the detent(s) can be attached to, or integral to, the housing 150, and the catch(es) can be attached to, or integral to, the guide element 160.

Figure 8:
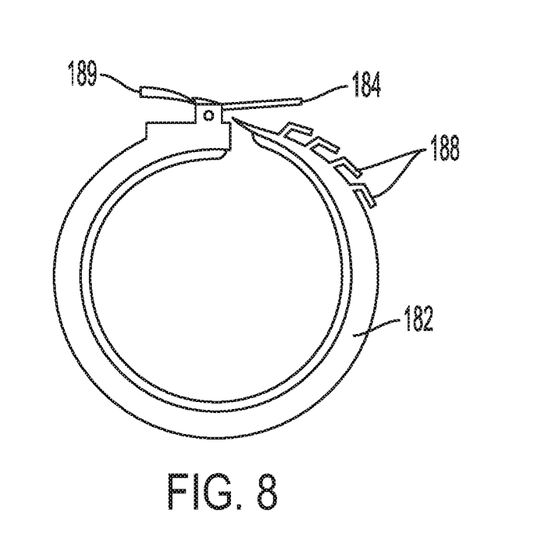
FIG. 8 is a top view of a locking mechanism of the assembly of FIG. 2.
Figure 9:
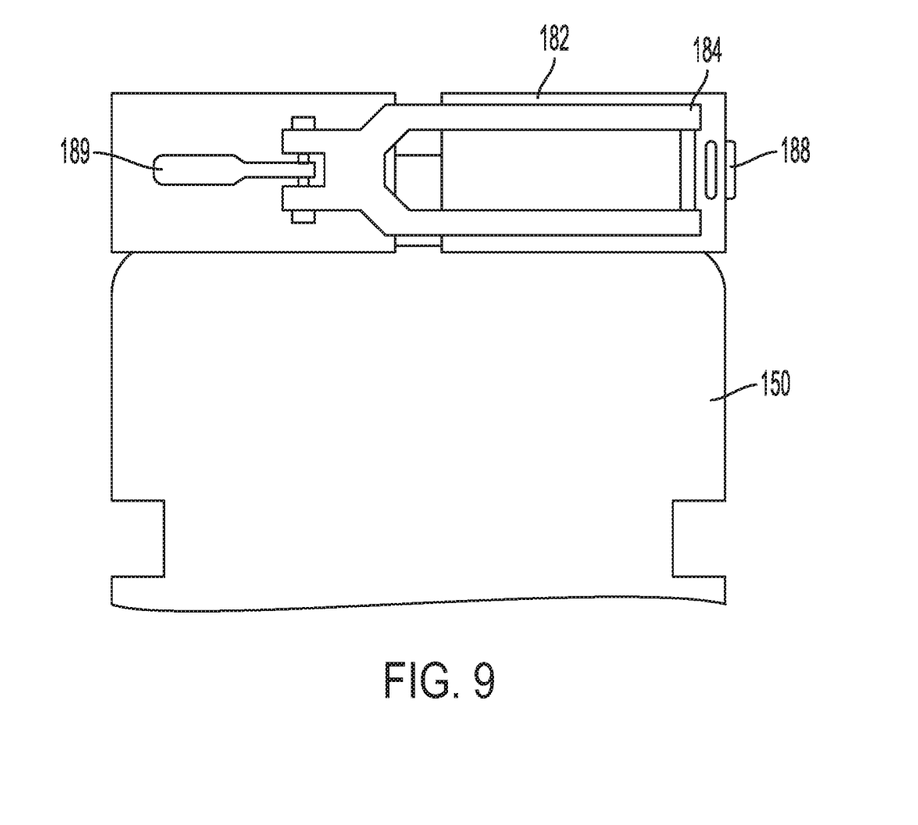
FIG. 9 is a partial side view of the assembly of FIG. 2, showing detail of the locking mechanism.
Figure 10:
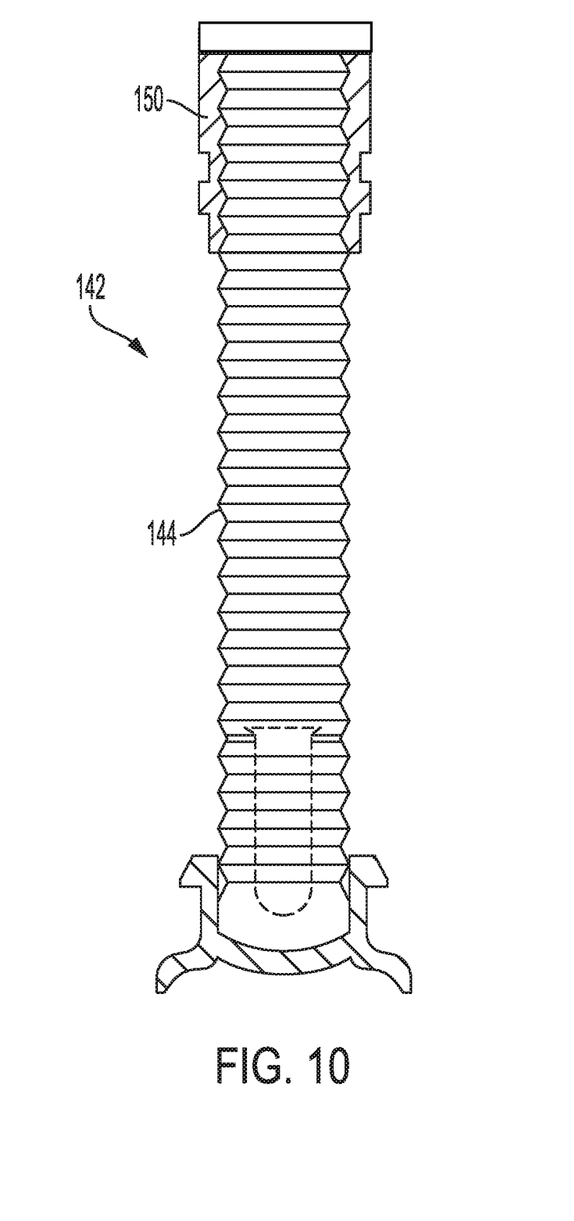
FIG. 10 is a side view of the assembly of FIG. 2 in an expanded configuration.

Referring to FIGS. 2, 8, and 9, the sterile probe cover assembly 100 can comprise a locking mechanism 180 that is configured to secure the sterile probe cover assembly 100 to the probe 10 (e.g., TEE probe). The locking mechanism 180 can comprise a band 182 having a pawl 184 at a first end 186 and a plurality of notches 188 that are configured to engage the pawl and are spaced along the length of the band. In some embodiments, the plurality of notches can comprise teeth that extend radially outward from the band. In further embodiments, the plurality of notches can comprise through holes that are configured to receive a hooked portion of the pawl 184. It should be understood that the pawl 184 need not require a spring bias to force the pawl 184 in contact with the notches 188. For example, in some embodiments, a medical professional can apply the force to move the pawl 184 into contact with the notches 188. The locking mechanism 180 can compress at least a portion of the housing 150 to cause an inner surface of the housing to frictionally engage an outer surface of the probe 10 (e.g., TEE probe). The pawl can have a release lever 189 that is configured to disengage the pawl 184 from the notches 188 to thereby release the sterile probe cover assembly from the probe. In other optional aspects, the locking mechanism can comprise a single notch. In various other embodiments, the locking mechanism 180 can comprise hook and loop fasteners, a pressure-sensitive adhesive, or any other suitable method for releasably affixing the housing 150 to the probe 10 (e.g., TEE probe).

Figure 14:
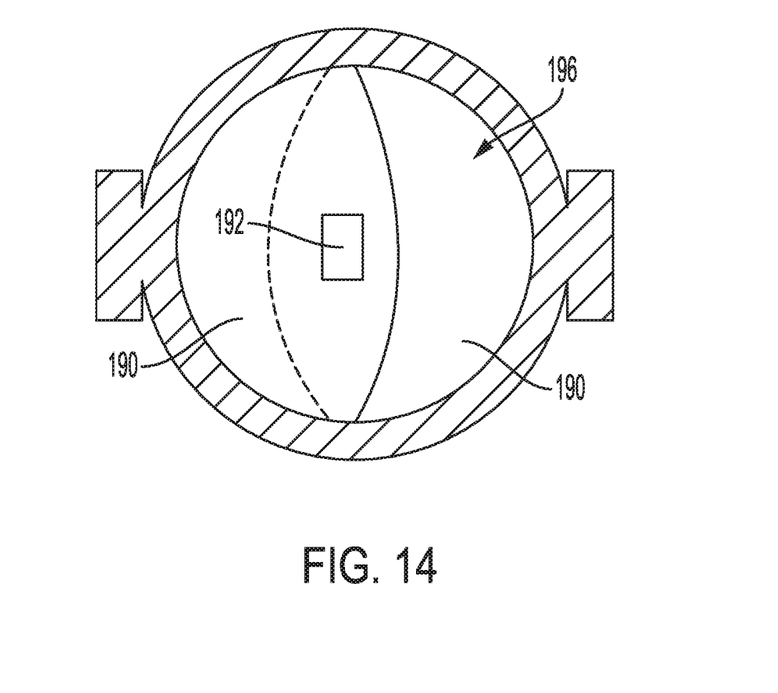
FIG. 14 is a bottom view of the assembly of FIG. 2.
Figure 15:
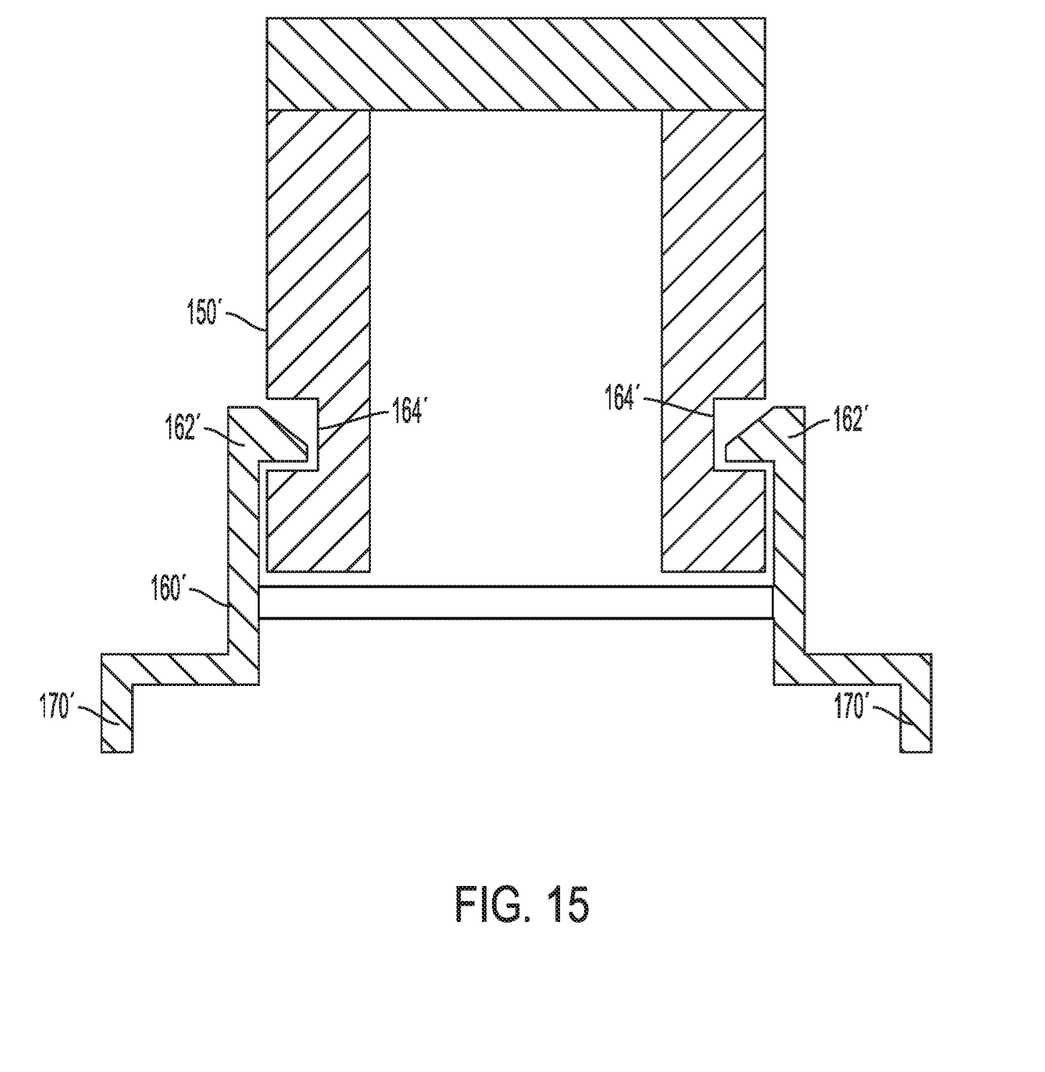
FIG. 15 is a side view of an alternative embodiment of a housing and a guide element in accordance with embodiments disclosed herein.

Referring to FIGS. 2 and 14, a distal opening 196 can be disposed at the distal end 104 of the cover 101. The distal (camera) end of the probe shaft 12 can extend through the distal opening 196 to expose the camera for insertion into the patient's mouth. In this way, the probe 10 does not need to be removed from the cover 101 during a procedure. A pair of overlapping flaps 190 can cover the distal opening 196 at the distal end 104 the cover 101. A fastener 192, such as hook and loop (e.g., VELCRO fastener), can attach the overlapping flaps 190 to each other in order to close off the opening 196. When used, the medical professional can grip the guide element 160 to retract the cover 101, thereby forcing the probe shaft 12 and gel capsule 120 through the distal opening 196. The flaps 190 and/or the guide element 120 can be flexible and resilient so that the flaps 190 can spread (thereby detaching the fastener 192) to allow the gel capsule 120 and distal end of the probe shaft 12 to extend through the distal opening 196. After the procedure, the medical professional can pull the guide element 160 back over the distal end of the probe shaft 12. The flaps 190 can resiliently close to cover the distal opening 196, thereby keeping the patient's bodily fluids within the cover and away from medical personnel. As the flaps 190 close, the fastener 192 can automatically engage.

Referring to FIGS. 1-15, before use, the sterile probe cover 101 can be stored in a sterile bag or container. The cover 101 can be stored in the collapsed configuration 140, as shown in FIG. 11. To use the sterile probe cover assembly 100, a medical professional can peel off the removable lid 132 from the gel capsule 120. Next, the medical professional can insert the gel capsule 120 into the cover 101. In further aspects, sterile probe cover assembly 100 can be provided with the gel capsule positioned within the cover 101. The bottom of the gel capsule can optionally extend to the bottom of the cover 101. The medical professional can then insert probe 10 into the gel capsule 120, and the cover 101 can be expanded to cover the length 14 of the probe shaft 12. The cover can be attached to the probe 10 via the locking mechanism 180 for sterile transportation. Once transported to the patient, the cover 101 can be retracted to expose the distal end of the probe shaft 12 through the distal opening 196. The cover can be collapsed until the guide element's detents (latches 162) engages the housing's catches 164. The gel capsule 120 can be removed from the end of the probe shaft 120 (and disposed of), leaving a layer of gel on the probe shaft 12. The probe 10 can be inserted into the patient's esophagus and used to capture images from the patient. After extraction from the patient, the probe 10 can then be replaced in the sterile probe cover assembly 100. The latches 162 can be disengaged from the catches 164, and the cover 101 can be expanded to again cover the probe shaft 12. The guide element 160 can be pulled until the cover 101 covers the distal end of the probe shaft 12 so that the flaps 190 close and the fastener 192 can secure the flaps 190 in place. After use and transportation to a proper location, the locking mechanism 180 can be disengaged, and the sterile probe cover assembly 100 can be disposed of. Accordingly, the sterile probe cover assembly 100 can be configured only for single use.

The sterile probe cover assembly as disclosed herein provides multiple advantages over conventional systems. One conventional system, the CIV-FLEX TEE probe cover, requires a medical professional to inject gel into a bottom of a narrow plastic bag portion of the CIV-FLEX TEE probe cover. The TEE probe is then inserted in to the narrow plastic bag portion of the CIV-FLEX TEE probe cover, and the bag is pulled over the probe shaft and then secured via tied string to the TEE probe. In contrast, the sterile probe cover assembly disclosed herein eliminates the need for injecting gel or adjusting and securing a bag in an unstable and unreliable way. The sterile probe cover assembly disclosed herein also improves the efficiency of the applying gel to the probe while also ensuring that sterility is maintained.

The sterile probe cover assembly as disclosed herein can be used to minimize contamination of the TEE probes for the safety of the patient as well as to prevent exposure of the patient's bodily fluids (e.g., blood, saliva, and mucus) to medical personnel. The sterile probe cover assembly 100 can further protect the TEE probe's delicate hardware, such as the camera, from physical damage. Moreover, the sterile probe cover assembly 100 as described herein can reduce the time required to prepare for a TEE procedure over conventional methods, which can be particularly desirable in emergency situations. Further, the disclosed sterile probe cover assembly 100 and, in particular, the pre-filled gel cartridge 120 can ensure a more uniform coverage than conventional systems, thereby rendering better quality imaging than conventional systems.

A kit can comprise a plurality of the sterile probe cover assemblies 100. The kit can further comprise a TEE probe.

Although disclosed herein with reference to use with probes (e.g., TEE probes), embodiments of the sterile probe cover assembly 100 are not limited to use with such probes, and it is contemplated that embodiments can be used with various elongated sterile equipment. Moreover, skilled artisans should understand that the embodiments disclosed herein can be modified, consistent with the disclosed aspects, for containment, protection, and sterile transportation of various elongated sterile equipment.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An assembly for receiving a transesophageal echocardiogram probe that comprises a probe shaft having a length, the assembly comprising: a cover defining an opening at a proximal end and a receiving space in communication with the opening, the receiving space having a length in a longitudinal dimension that is sufficient to receive the length of the probe shaft; a gel capsule positioned within the receiving space of the cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the probe shaft with a clearance to permit contact between the gel within the capsule and an exterior surface of the probe shaft.

Aspect 2: The assembly of aspect 1, wherein the cover is configured for selective elongation and retraction in the longitudinal dimension about and between a collapsed configuration and an expanded configuration.

Aspect 3: The assembly of aspect 1 or aspect 2, wherein the cover comprises an accordion fold structure.

Aspect 4: The assembly of any of the preceding aspects, wherein the cover comprises at least one gasket that engages an exterior surface of the gel capsule and is configured to hold the gel capsule in place in the longitudinal dimension with respect to the cover as the probe shaft is removed from the gel capsule.

Aspect 5: The assembly of any of the preceding aspects, wherein the gel capsule further comprises a removable lid.

Aspect 6: The assembly of any of the preceding aspects, further comprising a locking mechanism configured to secure the assembly to the TEE probe.

Aspect 7: The assembly of aspect 6, wherein the locking mechanism comprises a band having a pawl at a first end of the band and a plurality of notches spaced along the length of the band and configured to engage the pawl.

Aspect 8: The assembly of aspect 7, wherein the locking mechanism comprises a release lever that is configured to disengage the pawl from the notches.

Aspect 9: The assembly of any of the preceding aspects, further comprising a housing that is coupled to the cover at the proximal end of the cover, wherein the housing defines an interior volume that receives the cover in the collapsed configuration and the gel capsule within the cover.

Aspect 10: The assembly of aspect 9, further comprising a guide element that is coupled to the cover at a distal end of the cover, wherein one of the housing and the guide element comprises a detent, and the other of the housing and the guide element comprises a catch into which the detent is received so that the housing and guide element are configured to couple to one another via the detent.

Aspect 11: The assembly of aspect 9 or aspect 10, wherein the housing defines a cylindrical interior volume that has a length that is approximately the length of the cover in the collapsed configuration.

Aspect 12: The assembly of aspect 9, further comprising a locking mechanism, wherein the housing is configured to be coupled to the TEE probe via the locking mechanism.

Aspect 13: The assembly of aspect 12, wherein the locking mechanism comprises a band having a pawl at a first end of the band and a plurality of teeth spaced along the length of the band, wherein the locking mechanism engages the housing, and wherein the housing is flexible so that the housing is configured to compress as the band is ratcheted down against the housing and engage the probe.

Aspect 14: The assembly of any of aspects 9-13, wherein the housing and the cover collectively comprise a single monolithic component.

Aspect 15: The assembly of any of aspects 2-14, wherein, when the cover is in the collapsed configuration, the cover defines an interior volume that is approximately equal to the exterior volume of the gel capsule.

Aspect 16: The assembly of any of the preceding aspects, wherein the cover comprises an outer plastic layer and an inner sterile paper layer.

Aspect 17: A probe system comprising: a TEE probe; and an assembly as recited in any one of aspects 1-16.

Aspect 18: A kit comprising: a plurality of covers, each cover defining an opening at a proximal end and a receiving space in communication with the opening, the receiving space having a length in a longitudinal dimension that is sufficient to receive a length of a shaft of a TEE probe; and a plurality of gel capsules, each gel capsule configured to be positioned within the receiving space of a respective cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the shaft of the TEE probe with a clearance to permit contact between the gel within the capsule and an exterior surface of the shaft of the TEE probe.

Aspect 19: The kit of aspect 18, further comprising a TEE probe.

Aspect 20: A probe cover for receiving a transesophageal echocardiogram (TEE) probe that comprises a probe shaft having a length, the probe cover comprising: a collapsible structure configured to be expandable from a collapsed configuration to an expanded configuration, wherein the collapsible structure defines an opening at a proximal end and a receiving space in communication with the opening, wherein, when the collapsible structure is in the expanded configuration, the receiving space has a length in a longitudinal dimension that is sufficient to receive the length of the probe shaft, wherein the collapsible structure, when in the expanded configuration, is configured to receive a gel capsule.

Aspect 21: The probe cover of aspect 20, further comprising an elastic member configured to engage the gel capsule to retain the gel capsule within the collapsible structure.

Aspect 22: The probe cover of aspect 20 or aspect 21, wherein the collapsible structure has an accordion fold structure.

Aspect 23: The probe cover of any of aspects 20-23, further comprising a housing a housing that is coupled to the collapsible structure at the proximal end of the collapsible structure, wherein the housing defines an interior volume sufficient to receive the cover in the collapsed configuration and the gel capsule within the cover.

Aspect 24: The probe cover of aspect 23, further comprising a guide element that is coupled to the collapsible structure at a distal end of the cover, wherein one of the housing and the guide element comprises a detent, and the other of the housing and the guide element comprises a catch into which the detent is received so that the housing and guide element are configured to couple to one another via the detent.

Aspect 25: A method of using the probe system of aspect 17, comprising: inserting the gel capsule within the receiving space of the cover; inserting at least a distal portion of a shaft of the TEE probe into the interior of the gel capsule; expanding the cover to cover at least a length of the distal portion of the shaft of the TEE probe; retracting the cover to expose the gel capsule and the distal portion of the TEE probe; and moving the gel capsule to expose the distal portion of the TEE probe, wherein the distal portion of the TEE probe is coated with gel from within the interior of the gel capsule.

Aspect 26: The method of aspect 25, further comprising inserting the distal portion of the TEE probe within a patient.

Although the foregoing invention has been described in some detail by way of illustration and example for purposes of clarity of understanding, certain changes and modifications may be practiced within the scope of the appended claims.

What is claimed is:

1. An assembly for receiving a transesophageal echocardiogram (TEE) probe that comprises a probe shaft having a length, the assembly comprising:
   a cover defining an opening at a proximal end and a receiving space in communication with the opening, the receiving space having a length in a longitudinal dimension that is sufficient to receive the length of the probe shaft, wherein the cover is configured for selective elongation and retraction in the longitudinal dimension about and between a collapsed configuration and an expanded configuration;
   a gel capsule positioned within the receiving space of the cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the probe shaft with a clearance to permit contact between the gel within the capsule and an exterior surface of the probe shaft; and
   a housing that is attached to the cover at the proximal end of the cover, wherein the housing defines an interior volume sufficient to receive the cover in the collapsed configuration and the gel capsule within the cover.

2. The assembly of claim 1, wherein the cover comprises an accordion fold structure.

3. The assembly of claim 1, wherein the cover comprises at least one gasket that engages an exterior surface of the gel capsule and is configured to hold the gel capsule in place in the longitudinal dimension with respect to the cover as the probe shaft is removed from the gel capsule.

4. The assembly of claim 1, wherein the gel capsule further comprises a removable lid.

5. The assembly of claim 1, further comprising a locking mechanism configured to secure the assembly to the TEE probe.

6. The assembly of claim 5, wherein the locking mechanism comprises a band having a pawl at a first end of the band and a plurality of notches spaced along the length of the band and configured to engage the pawl.

7. The assembly of claim 6, wherein the locking mechanism comprises a release lever that is configured to disengage the pawl from the notches.

8. The assembly of claim 1, further comprising a guide element that is coupled to the cover at a distal end of the cover, wherein one of the housing and the guide element comprises a detent, and the other of the housing and the guide element comprises a catch into which the detent is received so that the housing and guide element are configured to couple to one another via the detent.

9. The assembly of claim 1, wherein the housing defines a cylindrical interior volume that has a length that is approximately equal to a length of the cover in the collapsed configuration.

10. The assembly of claim 1, further comprising a locking mechanism, wherein the housing is configured to be coupled to the TEE probe via the locking mechanism.

11. The assembly of claim 10, wherein the locking mechanism comprises a band having a pawl at a first end of the band and a plurality of notches spaced along the length of the band, wherein the locking mechanism engages the housing, and wherein the housing is flexible so that the housing is configured to compress as the band is ratcheted down against the housing and engage the probe.

12. The assembly of claim 1, wherein the housing and the cover are unitarily formed as a single monolithic component.

13. The assembly of claim 1, wherein, when the cover is in the collapsed configuration, the cover defines an interior volume that is approximately equal to an exterior volume of the gel capsule.

14. The assembly of claim 1, wherein the cover comprises an outer plastic layer and an inner sterile paper layer.

15. A probe system comprising:
a TEE probe comprising a probe shaft having a length, a distal end, and an exterior surface; and
an assembly as recited in claim 1, wherein the receiving space of the cover of the assembly receives the length of the probe shaft of the TEE probe, and wherein the cross sectional area of the interior of the gel capsule of the assembly receives the distal end of the probe shaft with a clearance to permit contact between the gel within the gel capsule and the exterior surface of the probe shaft.

16. A kit comprising:
a plurality of covers, each cover defining an opening at a proximal end and a receiving space in communication with the opening, wherein the cover is configured for selective elongation and retraction in a longitudinal dimension about and between a collapsed configuration and an expanded configuration, wherein, in the expanded configuration, the receiving space has a length in the longitudinal dimension that is sufficient to receive a length of a shaft of a TEE probe;
a plurality of gel capsules, each gel capsule configured to be positioned within the receiving space of a respective cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the shaft of the TEE probe with a clearance to permit contact between the gel within the capsule and an exterior surface of the shaft of the TEE probe; and
a plurality of housings, wherein each housing of the plurality of housings is attached to a respective cover of the plurality of the covers at the proximal end of the respective cover, wherein each housing defines an interior volume sufficient to receive within the interior volume the respective cover in the collapsed configuration and a respective gel capsule of the plurality of gel capsules.

17. A method of using a probe system, the probe system comprising:
a transesophageal echocardiogram (TEE) probe comprising a probe shaft having a length, a distal end, and an exterior surface;
an assembly for receiving the TEE probe, the assembly comprising:
a cover defining an opening at a proximal end and a receiving space in communication with the opening, the receiving space having a length in a longitudinal dimension that is sufficient to receive the length of the probe shaft; and
a gel capsule positioned within the receiving space of the cover, the gel capsule defining a proximal opening and an interior in communication with the proximal opening, wherein the interior of the gel capsule contains a quantity of gel, and wherein, within a plane that is perpendicular to the longitudinal dimension, the interior has a cross sectional area that is sufficient to receive a distal end of the probe shaft with a clearance to permit contact between the gel within the capsule and an exterior surface of the probe shaft,
wherein the receiving space of the cover of the assembly receives the length of the probe shaft of the TEE probe, and wherein the cross sectional area of the interior of the gel capsule of the assembly receives the distal end of the probe shaft with a clearance to permit contact between the gel within the gel capsule and the exterior surface of the probe shaft,
the method comprising:
inserting at least a distal portion of the probe shaft of the TEE probe into the interior of the gel capsule;
expanding the cover to cover at least a length of the distal portion of the probe shaft of the TEE probe;
retracting the cover to expose the gel capsule and the distal portion of the TEE probe; and
moving the gel capsule to expose the distal portion of the TEE probe, wherein the distal portion of the TEE probe is coated with gel from within the interior of the gel capsule.

18. The method of claim 17, further comprising inserting the distal portion of the TEE probe within a patient.

* * * * *